United States Patent
Sinz et al.

(10) Patent No.: US 10,509,049 B2
(45) Date of Patent: Dec. 17, 2019

(54) METHOD OF OPERATING A LABORATORY SAMPLE DISTRIBUTION SYSTEM, LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventors: Achim Sinz, Waiblingen (DE); Christian Riether, Muehltal (DE); Norbert Oranth, Voerstetten (DE); Martin Burri, Bettwil (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 201 days.

(21) Appl. No.: 15/455,773

(22) Filed: Mar. 10, 2017

(65) Prior Publication Data

US 2017/0184622 A1    Jun. 29, 2017

Related U.S. Application Data

(63) Continuation of application No. PCT/EP2015/071041, filed on Sep. 15, 2015.

(30) Foreign Application Priority Data

Sep. 15, 2014 (EP) .................................. 14184818

(51) Int. Cl.
*G01N 35/04* (2006.01)
*G01N 35/00* (2006.01)
*B65G 54/02* (2006.01)

(52) U.S. Cl.
CPC ............. *G01N 35/04* (2013.01); *B65G 54/02* (2013.01); *G01N 35/00693* (2013.01); *G01N 2035/0477* (2013.01)

(58) Field of Classification Search
CPC ... G01N 35/04; G01N 35/00693; B65G 54/02
See application file for complete search history.

(56) References Cited

U.S. PATENT DOCUMENTS

| 3,273,727 A | 9/1966 | Rogers et al. |
| 3,653,485 A | 4/1972 | Donlon |

(Continued)

FOREIGN PATENT DOCUMENTS

| CN | 201045617 Y | 4/2008 |
| CN | 102109530 A | 6/2011 |

(Continued)

OTHER PUBLICATIONS

International Search Report dated Jan. 12, 2016, in Application No. PCT/EP2015/071041, 4 pages.

*Primary Examiner* — Matthew D Krcha
(74) *Attorney, Agent, or Firm* — Roche Diagnostics Operations, Inc.

(57) ABSTRACT

A method of operating a laboratory sample distribution system is presented. The method comprises a number of sample container carriers on a transport plane by a number of electro-magnetic actuators. The method is adapted to compensate deviations regarding physical properties of the sample container carriers, the transport plane and the electro-magnetic actuators compared to reference components. A laboratory automation system comprising such a laboratory sample distribution system is also presented.

18 Claims, 2 Drawing Sheets

(56) References Cited

U.S. PATENT DOCUMENTS

| | | |
|---|---|---|
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,457,368 A | 10/1995 | Jacobsen et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 | 9/2014 | Stoeckle et al. |
| 8,973,736 B2 | 3/2015 | Johns et al. |
| 9,097,691 B2 | 8/2015 | Onizawa et al. |
| 9,211,543 B2 | 12/2015 | Ohga et al. |
| 9,423,410 B2 | 8/2016 | Buehr |
| 9,423,411 B2 | 8/2016 | Riether |
| 9,567,167 B2 | 2/2017 | Sinz |
| 9,575,086 B2 | 2/2017 | Heise et al. |
| 9,593,970 B2 | 3/2017 | Sinz |
| 9,618,525 B2 | 4/2017 | Malinowski et al. |
| 9,658,241 B2 | 5/2017 | Riether et al. |
| 2002/0009391 A1 | 1/2002 | Marquiss et al. |
| 2002/0028158 A1 | 3/2002 | Wardlaw |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234065 A1 | 8/2014 | Heise et al. |
| 2014/0234949 A1 | 8/2014 | Wasson et al. |
| 2014/0234978 A1 | 8/2014 | Heise et al. |
| 2015/0014125 A1 | 1/2015 | Hecht |
| 2015/0166265 A1 | 6/2015 | Pollack et al. |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276778 A1 | 10/2015 | Riether et al. |
| 2015/0276782 A1 | 10/2015 | Riether |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0077120 A1 | 3/2016 | Riether |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |

(56) References Cited

U.S. PATENT DOCUMENTS

| | | |
|---|---|---|
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |
| 2018/0128848 A1 | 5/2018 | Schneider et al. |
| 2018/0156835 A1 | 6/2018 | Hassan |
| 2018/0188280 A1 | 7/2018 | Malinowski |
| 2018/0210000 A1 | 7/2018 | van Mierlo |
| 2018/0210001 A1 | 7/2018 | Reza |
| 2018/0217174 A1 | 8/2018 | Malinowski |
| 2018/0217176 A1 | 8/2018 | Sinz et al. |
| 2018/0224476 A1 | 8/2018 | Birrer et al. |
| 2018/0348244 A1 | 12/2018 | Ren |
| 2018/0348245 A1 | 12/2018 | Schneider et al. |
| 2019/0018027 A1 | 1/2019 | Hoehnel |
| 2019/0076845 A1 | 3/2019 | Huber et al. |
| 2019/0076846 A1 | 3/2019 | Durco et al. |
| 2019/0086433 A1 | 3/2019 | Hermann et al. |
| 2019/0094251 A1 | 3/2019 | Malinowski |
| 2019/0094252 A1 | 3/2019 | Waser et al. |
| 2019/0101468 A1 | 4/2019 | Haldar |

FOREIGN PATENT DOCUMENTS

| | | | |
|---|---|---|---|
| DE | 3909786 A1 | | 9/1990 |
| DE | 10200505012 B | | 4/2007 |
| DE | 102005051012 B | | 4/2007 |
| DE | 102012000665 A1 | | 8/2012 |
| DE | 102011090044 A1 | | 7/2013 |
| EP | 0601213 A1 | | 10/1992 |
| EP | 0775650 A1 | | 5/1997 |
| EP | 0916406 A2 | | 5/1999 |
| EP | 1122194 A1 | | 8/2001 |
| EP | 1524525 A1 | | 4/2005 |
| EP | 2119643 A1 | | 11/2009 |
| EP | 2148117 A1 | | 1/2010 |
| EP | 2327646 A1 | | 6/2011 |
| EP | 2447701 A2 | | 5/2012 |
| EP | 2500871 A1 | | 9/2012 |
| EP | 2589966 A1 | | 5/2013 |
| EP | 2589966 A1 * | 5/2013 | ............ B65G 54/02 |
| EP | 2502675 B1 | | 2/2014 |
| EP | 2887071 A1 | | 6/2015 |
| GB | 2165515 A | | 4/1986 |
| JP | S56-147209 A | | 11/1981 |
| JP | 60-223481 A | | 11/1985 |
| JP | 61-081323 A | | 4/1986 |
| JP | S61-069604 A | | 4/1986 |
| JP | S61-094925 A | | 5/1986 |
| JP | S61-174031 A | | 8/1986 |
| JP | S61-217434 A | | 9/1986 |
| JP | S62-100161 A | | 5/1987 |
| JP | S63-31918 A | | 2/1988 |
| JP | S63-48169 A | | 2/1988 |
| JP | S63-82433 U | | 5/1988 |
| JP | S63-290101 A | | 11/1988 |
| JP | 1148966 A | | 6/1989 |
| JP | H01-266860 A | | 10/1989 |
| JP | H02-87903 A | | 3/1990 |
| JP | 03-112393 A | | 5/1991 |
| JP | 03-192013 A | | 8/1991 |
| JP | H03-38704 Y2 | | 8/1991 |
| JP | H04-127063 A | | 4/1992 |
| JP | H05-69350 A | | 3/1993 |
| JP | H05-142232 A | | 6/1993 |
| JP | H05-180847 A | | 7/1993 |
| JP | 06-26808 A | | 2/1994 |
| JP | H06-148198 A | | 5/1994 |
| JP | 06-156730 A | | 6/1994 |
| JP | 06-211306 A | | 8/1994 |
| JP | 07-228345 A | | 8/1995 |
| JP | 07-236838 A | | 9/1995 |
| JP | H07-301637 A | | 11/1995 |
| JP | H09-17848 A | | 1/1997 |
| JP | H11-083865 A | | 3/1999 |
| JP | H11-264828 A | | 9/1999 |
| JP | H11-304812 A | | 11/1999 |
| JP | H11-326336 A | | 11/1999 |
| JP | 2000-105243 A | | 4/2000 |
| JP | 2000-105246 A | | 4/2000 |
| JP | 2001-124786 A | | 5/2001 |
| JP | 2001-240245 A | | 9/2001 |
| JP | 2005-001055 A | | 1/2005 |
| JP | 2005-249740 A | | 9/2005 |
| JP | 2006-106008 A | | 4/2006 |
| JP | 2007-309675 A | | 11/2007 |
| JP | 2007-314262 A | | 12/2007 |
| JP | 2007-322289 A | | 12/2007 |
| JP | 2009-036643 A | | 2/2009 |
| JP | 2009-062188 A | | 3/2009 |
| JP | 2009-145188 A | | 7/2009 |
| JP | 2009-300402 A | | 12/2009 |
| JP | 2010-243310 A | | 10/2010 |
| JP | 2010-271204 A | | 12/2010 |
| JP | 2013-172009 A | | 2/2013 |
| JP | 2013-190400 A | | 9/2013 |
| SU | 685591 A1 | | 9/1979 |
| WO | 1996036437 A1 | | 11/1996 |
| WO | 2003042048 A3 | | 5/2003 |
| WO | 2007024540 A1 | | 3/2007 |
| WO | 2008133708 A1 | | 11/2008 |
| WO | 2009002358 A1 | | 12/2008 |
| WO | 2010042722 A1 | | 4/2010 |
| WO | 2012170636 A1 | | 7/2010 |
| WO | 2010087303 A1 | | 8/2010 |
| WO | 2010129715 A1 | | 11/2010 |
| WO | 2012/158520 A1 | | 11/2012 |
| WO | 2012158541 A1 | | 11/2012 |
| WO | 2013152089 A1 | | 10/2013 |
| WO | 2013169778 A1 | | 11/2013 |
| WO | 2013177163 A1 | | 11/2013 |
| WO | 2014059134 A1 | | 4/2014 |
| WO | 2014071214 A1 | | 5/2014 |
| WO | 2015/104263 A2 | | 7/2015 |

\* cited by examiner

METHOD OF OPERATING A LABORATORY SAMPLE DISTRIBUTION SYSTEM, LABORATORY SAMPLE DISTRIBUTION SYSTEM AND LABORATORY AUTOMATION SYSTEM

CROSS-REFERENCE TO RELATED APPLICATIONS

This application is a continuation of PCT/EP2015/071041, filed Sep. 15, 2015, which is based on and claims priority to EP 14184818.4, filed Sep. 15, 2014, which is hereby incorporated by reference.

BACKGROUND

The present disclosure relates to a method of operating a laboratory sample distribution system, a laboratory sample distribution system and a laboratory automation system.

Known laboratory sample distribution systems are typically used in laboratory automation systems in order to distribute samples contained in sample containers between different laboratory stations. A typical laboratory sample distribution system can provide high throughput and reliable operation.

However, there is a need for a method of operating a laboratory sample distribution system that provides reliable, long term operation.

SUMMARY

According to the present disclosure, a method of operating a laboratory sample distribution system is disclosed. The laboratory sample distribution system can comprise a number of sample container carriers. The sample container carriers can each comprise at least one magnetically active device and can be adapted to carry at least one sample container. The laboratory sample distribution system can also comprise a transport plane adapted to support the sample container carriers and a number of electro-magnetic actuators stationary arranged below the transport plane. The electro-magnetic actuators can be adapted to move a corresponding sample container carrier on top of the transport plane by applying a magnetic force to the sample container carrier. The method can comprise activating one of the number electro-magnetic actuators to apply a magnetic force to one of the number of sample container carriers in order to cause a movement of the one sample container carrier, detecting an electro-magnetic actuator calibration movement profile of the one sample container carrier, determining at least one electro-magnetic actuator calibration parameter for the one electro-magnetic actuator in response to the electro-magnetic actuator calibration movement profile, and operating the one electro-magnetic actuator according to the at least one determined electro-magnetic actuator calibration parameter, when the one electro-magnetic actuator is activated a next time.

Accordingly, it is a feature of the embodiments of the present disclosure to provide a method of operating a laboratory sample distribution system that provides for a reliable long term operation. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
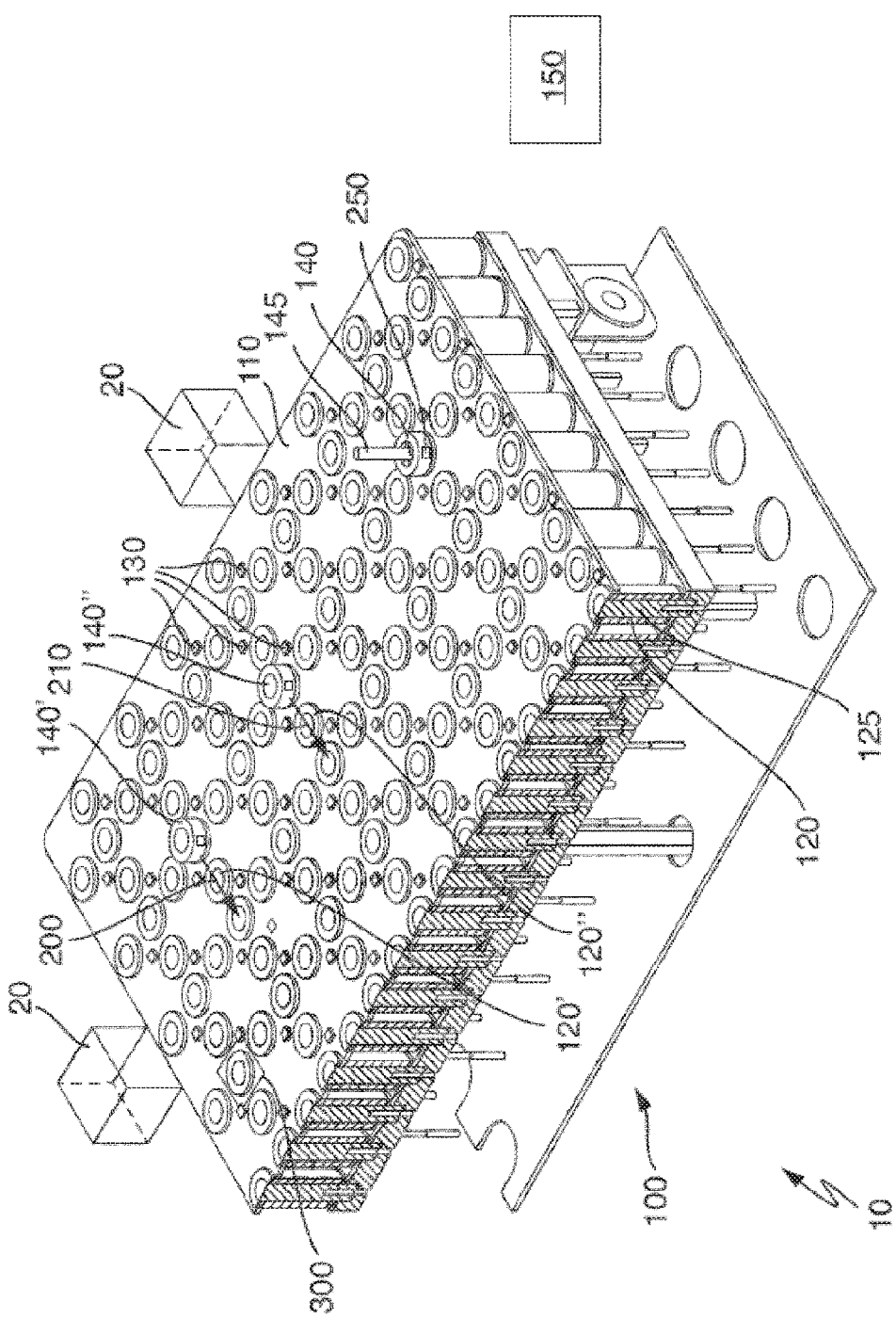
FIG. 1 illustrates a laboratory automation system comprising a laboratory sample distribution system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method of operating a laboratory sample distribution system is disclosed. The laboratory sample distribution system can comprise a number of sample container carriers. Each sample container carrier can comprise at least one magnetically active device. Each sample container carrier can be adapted to carry at least one sample container. The laboratory sample distribution system can further comprise a transport plane adapted to support or carry the sample container carriers. The laboratory sample distribution system can further comprise a number of electro-magnetic actuators. The electro-magnetic actuators can be stationary arranged below the transport plane and can be adapted to move a corresponding sample container carrier on top of the transport plane by applying a magnetic force to the sample container carrier.

The method can comprise the step a) of activating one or more of the number of electro-magnetic actuators to apply or exert or cause a magnetic force to one of the number of sample container carriers in order to induce a movement of the one sample container carrier. The method can further comprise the step b) of detecting an electro-magnetic actuator calibration movement profile of the one sample container carrier. The method can further comprise the step c) of determining at least one electro-magnetic actuator calibration parameter for the one electro-magnetic actuator in response to the electro-magnetic actuator calibration movement profile. The method can further comprise the step d) of operating the one electro-magnetic actuator according to the at least one determined electro-magnetic actuator calibration parameter.

A magnetic field strength of the one electro-magnetic actuator may deviate from a reference magnetic field strength of a reference or "normal" electro-magnetic actuator or from an average magnetic field strength of the rest of electro-magnetic actuators, in particular a selection of electro-magnetic actuators. If the electrical resistance of the one electro-magnetic actuator differs from the electrical resistance of the reference electro-magnetic actuator, a current flow caused by a driving voltage through the one electro-magnetic actuator may deviate from a current flow caused by a similar driving voltage through the reference electro-magnetic actuator and hence the magnetic fields generated by the respective current flows may differ. Reasons for this may be for example assembly margins, wear or damage. Additionally, surface properties of a local area of the transport plane, wherein the one electro-magnetic actuator can be arranged below the local area, may deviate from reference or "normal" surface properties of a reference local area. Surface properties can be for example a surface roughness of the local area or material on the local area. Reasons for this may be for example assembly margins, wear, damage, environment and dirt like a spilt sample. A magnetic field strength deviation of the one electro-magnetic actuator and surface properties deviations of the local area may cause a deviation of the movement of the one sample container carrier compared to a reference or "normal" movement. This may render the laboratory sample distribution system itself unreliable or it may limit the maximum driving potential of the laboratory sample distribution system. Alternatively or additionally, it may help to distinguish components of the laboratory sample distribution system, that may be replaced soon e.g. due to abrasion.

By the method of operating the laboratory sample distribution system, it can be possible to compensate deviations regarding physical properties of components of the laboratory sample distribution system, i.e. a magnetic field strength deviation of the one electro-magnetic actuator and surface properties deviations of the local area, without using an external inspection probe adapted for measurements of the physical properties. Hence, the one sample container carrier may be moved on the local area by the one electro-magnetic actuator according to the optimum target movement. Thus, for example, irregularities in a ride of the one sample container carrier may be prevented, which could otherwise cause a disruption in the operation of the laboratory sample distribution system. Hence, a maximum reliability and uptime of the laboratory sample distribution system can be ensured. The method may be performed, or executed, at startup of the laboratory sample distribution system and/or at intervals e.g. once a day. A measurement of the named properties with the external inspection probe may in some cases even not be possible, because the laboratory sample distribution system may be covered and hence not easily accessible. Additionally, such an inspection may require shutting down the laboratory sample distribution system at least partially.

The sample containers can typically be designed as tubes made of glass or transparent plastic and typically can have an opening at an upper end. The sample containers can be used to contain, store and transport samples such as blood samples or chemical samples. The transport plane can also be denoted as transport surface. The transport plane can support the sample container carriers, what can also be denoted as carrying the sample container carriers. The electro-magnetic actuators can typically be solenoids surrounding ferromagnetic cores. These electro-magnetic actuators may be energized in order to provide a magnetic field that can be used to move or drive the sample container carriers. For that purpose, the at least one magnetically active device in each sample container carrier may be a permanent magnet. Alternatively or additionally, an electro-magnet and/or any magnetically soft material can be used. The sample container carriers can typically be adapted to move in two dimensions on the transport plane. For that purpose, the electro-magnetic actuators may be arranged in two dimensions below the transport plane. The electro-magnetic actuators may be arranged in a grid or matrix having rows and columns along which the electro-magnetic actuators can be arranged.

The one sample container carrier, to which the magnetic force is applied in step a), can be within an operating distance of the one electro-magnetic actuator of interest, in order to induce a movement of the one sample container carrier. Activating the one electro-magnetic actuator can mean that a magnetic field can be generated by the one electro-magnetic actuator. Activating may be done by supplying a driving voltage from an electric power supply to the solenoid surrounding the ferromagnetic core. The electro-magnetic actuator calibration movement profile of the one sample container carrier in step b) can be a position (x/y) or a speed and a direction of the one sample container carrier over time, detected in order to determine the at least one electro-magnetic actuator calibration parameter for the one electro-magnetic actuator in step c). The position of the one sample container carrier may be detected by a plurality of sensors, e.g. Hall-sensors, of a control unit, the plurality of Hall-sensors arranged in a grid or matrix having rows and columns and each adapted to sense the presence of the at least one magnetically active device of the one sample container carrier. From the known position of the Hall-sensor, above which the one sample container carrier can be located, the position of the one sample container carrier may be deduced. Additionally or alternatively, the position of the one sample container carrier may be detected by a camera or another kind of sensor like an optical sensor of the control unit. Determining the at least one electro-magnetic actuator calibration parameter for the one electro-magnetic actuator in response to the electro-magnetic actuator calibration movement profile of the one sample container carrier in step c) may comprise comparing the electro-magnetic actuator calibration movement profile to a reference electro-magnetic actuator calibration movement profile for the one sample container carrier, e.g. a movement profile of the one sample container carrier caused by a reference electro-magnetic actuator measured in the past at a manufacturer's site. According to the at least one determined electro-magnetic actuator calibration parameter, the one electro-magnetic actuator can be operated in step d), when the one electro-magnetic actuator can be activated a next time, that can be in the following or consecutive activations, to apply a magnetic force to the one sample container carrier in order to induce a movement of the one sample container carrier. Hence, a magnetic field strength deviation of the one electro-magnetic actuator and surface properties deviations of the local area may be compensated.

The steps a) to d) can be performed or executed in the mentioned order. However, the determination of the at least one electro-magnetic actuator calibration parameter may be done in real-time, while the one sample container carrier is still moving, e.g. while the one sample container carrier is attracted by the one electro-magnetic actuator. When the one sample container is above the one electro-magnetic actuator, the polarity of the magnetic field caused by the one electro-magnetic actuator may be reversed and for a magnitude of a reversed driving voltage the at least one electro-magnetic actuator calibration parameter may be already considered.

The method may comprise the steps of storing the at least one electro-magnetic actuator calibration parameter for the one electro-magnetic actuator in a software of the control unit of the laboratory sample distribution system after step c) and reading the at least one electro-magnetic actuator calibration parameter before step d).

According to an embodiment, the steps a) to d) can be executed or repeated or performed for each of the number of electro-magnetic actuators. For example, the number of electro-magnetic actuators may differ from each other in their magnetic strength and a number of local areas of the transport plane may differ from each other in their surface properties. Each of the number of local areas can be allocated to a particular electro-magnetic actuator of the number of electro-magnetic actuators arranged below the respective local area. Differences between the magnetic field strength of the number of electro-magnetic actuators and differences between the surface properties of the number of local areas of the transport plane may be compensated, such that the one sample container carrier may be smoothly moved on the transport plane, no matter on which local area the one sample container carrier is located or positioned or moving.

According to an embodiment, the at least one electro-magnetic actuator calibration parameter can comprise a first electric power supply parameter of the one electro-magnetic actuator. In step d), the one electro-magnetic actuator can be supplied with electric power according to the first electric power supply parameter. The first electric power supply parameter may comprise or be incorporated as a magnitude of the driving voltage used to supply the one electro-magnetic actuator with electric power. Additionally or alternatively, the first electric power supply parameter may comprise or be incorporated as a potentiometer ratio of an adjustable potentiometer interconnected in between the electro-magnetic actuator and the power supply.

According to an embodiment, the at least one electro-magnetic actuator calibration parameter can comprise a first activating time duration parameter of the one electro-magnetic actuator and in step d), the one electro-magnetic actuator can be activated according to the first activating time duration parameter. The electric power supply may not have to be adjusted or may not be adjustable. In this case, a duration, during which the one electro-magnetic actuator can be activated, and hence the time duration, during which a magnetic force can be applied to the one sample container carrier, can be adjusted according to the first activating time duration parameter.

According to an embodiment, the method can comprise the step of disqualifying the one electro-magnetic actuator, if the at least one electro-magnetic actuator calibration parameter exceeds a specified electro-magnetic actuator parameter threshold value and/or if a change of the at least one electro-magnetic actuator calibration parameter between at least two consecutive executions or performances of the steps a) to c) exceeds a specified electro-magnetic actuator parameter change limit. The electro-magnetic actuator parameter threshold value may be an upper threshold value or a lower threshold value. Alternatively, an upper threshold value and a lower threshold value may define an electro-magnetic actuator parameter range. The one electro-magnetic actuator can be disqualified, if the at least one electro-magnetic actuator calibration parameter is outside of the electro-magnetic actuator calibration parameter range. A too high, too low or strongly changing electro-magnetic actuator calibration parameter can be an indication of a problem with the one electro-magnetic actuator or the local area, e.g. the one electro-magnetic actuator or its electric power supply may be going defect or the local area may be polluted, e.g. by spilled liquid from a liquid sample. Hence, the problem may be detected before the operation of the laboratory sample distribution system gets interrupted by the problem.

According to an embodiment, the method can comprise the following steps during operating the one electro-magnetic actuator according to step d): e) detecting a sample container carrier calibration movement profile of one of the number of sample container carriers, f) determining at least one sample container carrier calibration parameter for the one sample container carrier in response to the sample container carrier calibration movement profile, and g) operating the one electro-magnetic actuator according to the at least one determined electro-magnetic actuator calibration parameter and additionally to the at least one determined sample container carrier calibration parameter. The steps e) to f) can be performed or executed in the mentioned order. The sample container carrier calibration movement profile of the one sample container carrier in step e) can be a position or a speed and a direction of the one sample container carrier over time, detected in order to determine the at least one sample container carrier calibration parameter for the sample container carrier in step f).

Not only may the magnetic field strength of each of the number of electro-magnetic actuators and the surface properties of each of the number of local areas deviate from respective target values, also, the magnetic field strength of the at least one magnetically active device of each of the number of sample container carriers may deviate from a target magnetic field strength. Additionally, surface properties of a glide surface, with which each of the number of sample container carriers touches the transport plane, may deviate from target surface properties. After each of the number of electro-magnetic actuators at least one electro-magnetic actuator calibration parameter has been determined, for example, by the use of a particular reference sample container carrier, the steps e) to f) may be performed for all other sample container carriers of the number of sample container carriers. The steps e) to f) may be performed for sample container carriers that do not carry sample containers at that time, whereby the sample container carriers can be in a defined state, because different sample containers may have different weights. In case the at least one magnetically active device is an electro-magnet, in step g) additionally or alternatively, the electro-magnet may be operated according to the at least one determined sample container carrier calibration parameter. Hence, the one sample container carrier may be moved on the local area by the one electro-magnetic actuator according to the optimum target movement. Some of the sample container carriers can be removed from the laboratory sample distribution system for an external inspection, but this can mean that they may not be available during the time of the inspection and hence the number of sample container carriers had to be increased to compensate the missing ones.

The method may comprise the steps of storing the at least one sample container carrier calibration parameter of each of the number of sample container carriers in the software of the control unit of the laboratory sample distribution system after step f) and reading the at least sample container carrier calibration parameter before step g). According to an embodiment, each of the number of sample container carriers can comprise a sample container carrier calibration parameter memory unit and the method can comprise the steps of storing the at least one sample container carrier calibration parameter of each of the number of sample container carriers on the corresponding sample container carrier calibration parameter memory unit and reading the at least one sample container carrier calibration parameter from the sample container carrier calibration parameter memory unit. These two steps may be performed after step f) and before step g). The sample container carrier calibration parameter memory unit may be a non-volatile memory device. Hence, it can be possible to take a particular sample container carrier out of the laboratory sample distribution system and to put it into another, similar laboratory sample distribution system without losing the at least one sample container carrier calibration parameter for the particular sample container carrier and not having to perform the steps e) to f) again. Advantageously, each of the number of sample container carriers can comprise a receiving and sending unit and the control unit can comprise a receiving and sending unit in order to store the at least one sample container carrier calibration parameters on the sample container carriers and to read them from the sample container carriers.

According to an embodiment, the at least one sample container carrier calibration parameter can comprise a second electric power supply parameter of the one electro-magnetic actuator and, in step g), the electro-magnetic actuator can be supplied with electric power according to the second electric power supply parameter.

According to an embodiment, the at least one sample container carrier calibration parameter can comprise a second activating time duration parameter of the one electro-magnetic actuator and, in step g), the electro-magnetic actuator can be supplied with electric power according to the second activating time duration parameter.

According to an embodiment, the method can comprise the step of disqualifying the one sample container carrier, if the at least one sample container carrier calibration parameter exceeds a specified sample container carrier parameter threshold value and/or if a change of the at least one sample container carrier calibration parameter between at least two consecutive executions or performances of the steps e) to f) exceeds a specified sample container carrier parameter change limit. The sample container carrier threshold value may be an upper threshold value or a lower threshold value. Alternatively, an upper threshold value and a lower threshold value may define a sample container carrier parameter range. The one sample container carrier can be disqualified, if the at least one sample container carrier calibration parameter is outside of the sample container carrier calibration parameter range. A too high, too low or strongly changing sample container carrier calibration parameter is an indication of a problem with the one sample container carrier, e.g. the at least one magnetically active device may be defect or on the glide surface a liquid sample may be spilt, polluting the glide surface. Hence, the problem may be detected, before the operation of the laboratory sample distribution system gets interrupted by the problem.

A laboratory sample distribution system adapted to perform the method as described above is presented. The laboratory sample distribution system can comprise a number of sample container carriers. The sample container carriers can each comprise at least one magnetically active device such as, for example, at least one permanent magnet, and adapted to carry at least one sample container. The laboratory sample distribution system can also comprise a transport plane adapted to support said sample container carriers and a number of electro-magnetic actuators stationary arranged below the transport plane. The electro-magnetic actuators can be adapted to move a corresponding sample container carrier on top of the transport plane by applying a magnetic force to the sample container carrier. The laboratory sample distribution system can also comprise a control unit. The control unit can be adapted to activate one of the number of electro-magnetic actuators to apply a magnetic force to one of the number of sample container carriers in order to cause a movement of the one sample container carrier, to detect an electro-magnetic actuator calibration movement profile of the one sample container carrier, to determine at least one electro-magnetic actuator calibration parameter for the one electro-magnetic actuator in response to the electro-magnetic actuator calibration movement profile and to operate the one electro-magnetic actuator according to the at least one determined electro-magnetic actuator calibration parameter. Additionally, during operating the one electro-magnetic actuator according to the at least one determined electro-magnetic actuator calibration parameter, the control unit may be adapted to detect a sample container carrier calibration movement profile of one of the number of sample container carriers, to determine at least one sample container carrier calibration parameter for the one sample container carrier in response to the sample container carrier calibration movement profile and to operate the one electro-magnetic actuator according to the at least one determined sample container carrier calibration parameter. The control unit may further be adapted to disqualify the one electro-magnetic actuator and the one sample container carrier. Hence, the method can be automatically controlled by the control unit in a comfortable, fast and fail-safe manner. Additionally, the control unit can be capable of controlling several steps of several electro-magnetic actuators and several sample container carriers at a time.

In one embodiment, each of the number of sample container carriers can comprise a sample container carrier calibration parameter memory unit for the at least one sample container carrier calibration parameter. Advantageously, each of the number of sample container carriers can comprise a receiving and sending unit and the control unit can comprise a receiving and sending unit in order to store the at least one sample container carrier calibration parameters on the sample container carriers and to read them from the sample container carriers.

A laboratory automation system is also presented. The laboratory automation system can comprise a number of a pre-analytical, analytical and/or post-analytical laboratory stations and a laboratory sample distribution system as described above adapted to distribute the sample container carriers and/or sample containers between the laboratory stations.

The laboratory stations may be arranged adjacent to the laboratory sample distribution system. Pre-analytical stations may be adapted to perform any kind of pre-processing of samples, sample containers and/or sample container carriers. Analytical stations may be adapted to use a sample or part of the sample and a reagent to generate a measuring signal, the measuring signal indicating if and in which concentration, if any, an analyte exists. Post-analytical stations may be adapted to perform any kind of post-processing of samples, sample containers and/or sample container carriers. The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

Referring initially to FIG. 1, FIG. 1 shows a laboratory automation system 10 comprising a laboratory sample distribution system 100 and a number of pre-analytical, analytical and/or post-analytical laboratory stations 20 arranged adjacent to the laboratory sample distribution system 100. Self-evidently, more than the two laboratory stations 20 depicted in FIG. 1 may be comprised in the laboratory automation system 10.

The laboratory sample distribution system 100 can comprise a transport plane 110, under which a plurality of electro-magnetic actuators 120, 120', 120" can be positioned. The electro-magnetic actuators 120, 120', 120" can be implemented as solenoids having a solid ferromagnetic core 125. The electro-magnetic actuators 120, 120', 120" can be quadratically arranged in a grid or matrix having rows and columns. In each center of a quadrat formed by corresponding electro-magnetic actuators 120, 120', 120" no electro-magnetic actuator may be arranged. The transport plane can be divided in local areas 300. Under each local area 300, one of the electro-magnetic actuators 120, 120', 120" can be arranged, except for a selection of local areas 300, which can be arranged above the center of the quadrats formed by the corresponding electro-magnetic actuators 120, 120', 120".

Sample container carriers 140, 140', 140" can be positioned on the transport plane 110 and can be moved by the electro-magnetic actuators 120, 120', 120" on individual transport paths. While it can be understood that a plurality of sample container carriers 140, 140', 140" can be positioned on the transport plane 110, due to simplicity only three sample container carriers 140, 140', 140" are depicted in FIG. 1. The sample container carrier 140 can hold a sample container 145, in which a sample to be analyzed may be contained. Each of the sample container carriers 140, 140', 140" can comprise a not-shown permanent magnet.

The laboratory sample distribution system 100 can be adapted to distribute the sample container carriers 140, 140', 140" and/or the sample containers 145 between the laboratory stations 20. The laboratory stations 20 can be positioned adjacent to the transport plane 110 such that a sample container carrier 140, 140', 140" can be used to transport a sample contained in the sample container 145 to a respective laboratory station 20.

The laboratory sample distribution system 100 can further comprise a control unit 150. The control unit 150 can be configured to control movements of the sample container carriers 140, 140', 140" on the transport plane by activating and controlling the electro-magnetic actuators 120, 120', 120" such that the sample container carriers 140, 140', 140" independently and simultaneously can move along corresponding transport paths.

A plurality of Hall-sensors 130 can be arranged such that positions of respective sample container carriers 140, 140', 140" on the transport surface 110 can be detected.

Sample container carrier 140' can be a reference sample container carrier. A reference electro-magnetic actuator calibration movement profile and a reference sample container carrier calibration movement profile has been determined for the reference sample container carrier 140' caused by reference electro-magnetic actuators arranged below a reference transport plane measured in the past at a manufacturer's site.

Figure 2:
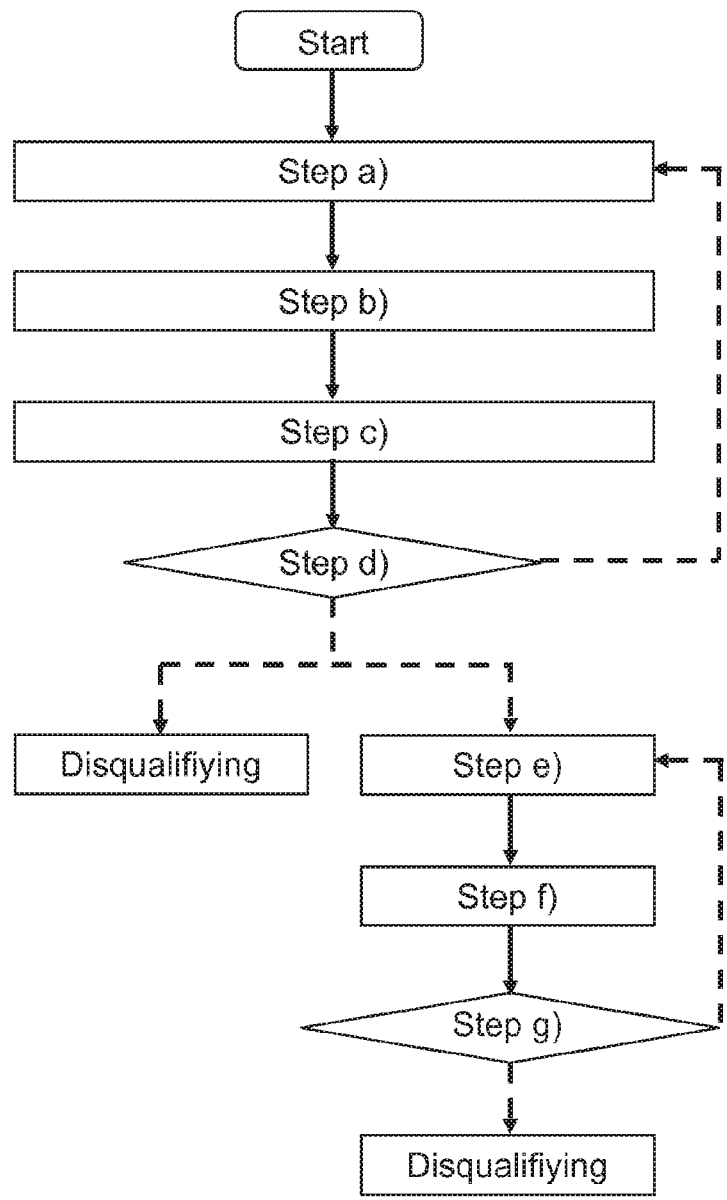
FIG. 2 illustrates a method of operating the laboratory automation system of FIG. 1 according to an embodiment of the present disclosure.

In FIG. 1, the reference sample container carrier 140' can be successively attracted by the electro-magnetic actuators 120, 120' arranged below the left part of the transport plane 110 and hence moved downwards in FIG. 1 as denoted by the arrow 200. This action can correspond to step a) in FIG. 2. For the electro-magnetic actuators 120, 120' arranged below the left part of the transport plane 110, no electro-magnetic actuator calibration parameters have been determined until then. The position of the reference sample container carrier 140' can be detected by the Hall-sensors 130. The position over time and hence the electro-magnetic actuator calibration movement profile of the reference sample container carrier 140' can be detected by the control unit 150. This action can correspond to step b) in FIG. 2. The control unit 150 can compare the electro-magnetic actuator calibration movement profile of the reference sample container carrier 140' to the target electro-magnetic actuator calibration movement profile and determines electro-magnetic actuator calibration parameters for the electro-magnetic actuators 120, 120' arranged below the left part of the transport plane 110. This action can correspond to step c) in FIG. 2.

The determined electro-magnetic actuator calibration parameters for the electro-magnetic actuators 120, 120' arranged below the left part of the transport plane 110 can be stored in a non-volatile storage of the control unit 150. When the electro-magnetic actuators 120, 120' are activated a next time, the electro-magnetic actuator calibration parameters can be read and the electro-magnetic actuators 120, 120' can be operated accordingly. This action can correspond to step d) in FIG. 2.

For example, the magnetic field of the electro-magnetic actuator 120' next to the reference sample container carrier 140' may be lower than a target magnetic field of the reference electro-magnetic actuators, and hence the reference sample container carrier 140' can be attracted by a magnetic force smaller than a reference magnetic force. Hence, the reference sample container carrier 140' may arrive later in time above the electro-magnetic actuator 120' than scheduled for a strong enough magnetic field of the electro-magnetic actuator 120'. From the deviation in time, the electro-magnetic actuator calibration parameter can be deduced. In this case, the electro-magnetic actuator calibration parameter can comprise a first electric power supply parameter. The electro-magnetic actuator 120' in FIG. 1 can be activated by supplying a default driving voltage from a not-shown electric power supply. If the magnetic field of the electro-magnetic actuator 120' were similar to the target magnetic field, the first electric power supply parameter can be one. Since the magnetic field of the electro-magnetic actuator 120' is lower than desired, the first electric power supply parameter can have a value larger than one, i.e. when the electro-magnetic actuator 120' is activated a next time, the electro-magnetic actuator calibration parameter can be read and the electro-magnetic actuator 120' can be supplied with the default driving voltage multiplied by the first electric power supply parameter, a current flow through the electro-magnetic actuator 120' can be larger and hence the magnetic field of the electro-magnetic actuator 120' can be larger.

If a value of one of the determined electro-magnetic actuator calibration parameters for the electro-magnetic actuators 120, 120' arranged below the left part of the transport plane 110 exceeds a specified electro-magnetic actuator parameter threshold value, e.g. the value two, the corresponding electro-magnetic actuator 120, 120' can be disqualified. This step can be optional as indicated by a dashed arrow in FIG. 2. For example, the control unit 150 can report an error message about the particular one electro-magnetic actuator 120, 120' to a human operator of the laboratory automation system 10.

For the electro-magnetic actuators 120, 120" arranged below the middle part and right part of the transport plane 110, electro-magnetic actuator calibration parameters have already been determined. However, for the sample container carrier 140" positioned in the middle part of the transport plane 110 no sample container carrier calibration parameter has been determined until then. The sample container carrier 140" can be successively attracted by the electro-magnetic actuators 120, 120" arranged below the middle part of the transport plane 110 and hence moved downwards in FIG. 1 as denoted by the arrow 210. Thereby, the electro-magnetic actuators 120, 120" arranged below the middle part of the transport plane 110 can be operated according to their already determined electro-magnetic actuator calibration parameters. This action can correspond to step d) in FIG. 2. The position over time and hence the sample container carrier calibration movement profile of the sample container carrier 140" can be detected by the control unit 150. This action can correspond to step e) in FIG. 2. The calibration of the sample container carrier 140" can be optional as indicated by a dashed arrow in FIG. 2. The control unit 150 can compare sample container carrier calibration movement profile of the sample container carrier 140" to the target sample container carrier calibration movement profile and can determine a sample container carrier calibration parameter for the sample container carrier 140". This action can correspond to step f) in FIG. 2.

The determined sample container carrier calibration parameter for the sample container carrier 140" can be wireless transferred from the control unit 150 to a receiving, sending and sample container carrier calibration parameter memory unit 250 of the sample container carrier 140". Each of the sample container carriers 140, 140', 140" can be individually addressable. Before the sample container carrier 140" is moved a next time, the sample container carrier calibration parameter can be read from the sample container carrier 140" and the electro-magnetic actuators 120, 120', 120" can be operated accordingly. This action can correspond to step g) in FIG. 2.

For example, the magnetic field of the permanent magnet of the sample container carrier 140" may be lower than a target magnetic field of the sample container carrier 140', and hence the sample container carrier 140" can be attracted by a magnetic force smaller than a target magnetic force. Hence, the sample container carrier 140" can arrive later in time above the electro-magnetic actuator 120" than scheduled for a strong enough magnetic field of the permanent magnet of the sample container carrier 140". From the deviation in time, the sample container carrier calibration parameter can be deduced. In this case, the sample container carrier calibration parameter can comprise a second electric power supply parameter, which can have the value one for no time deviation, but can have a value larger than one because of the late arrival. When the electro-magnetic actuator 120" is activated a next time to attract the sample container carrier 140", the sample container carrier calibration parameter can be read and the electro-magnetic actuators 120" can be supplied with electric energy with the magnitude of the last time multiplied by the second electric power supply parameter, i.e. the default driving voltage multiplied by the first electric power supply parameter and the second electric power supply parameter.

If the determined sample container carrier calibration parameter for the sample container carrier 140" exceeds a specified sample container carrier parameter threshold value, e.g. two, the sample container carrier 140" can be disqualified. This action can be optional as indicated by a dashed arrow in FIG. 2. For example, the control unit 150 can report an error message about the sample container carrier 140" to a human operator of the laboratory automation system 10.

For the sample container carrier 140 on the right part of the transport plane 110, a sample container carrier calibration parameter has already been determined. The electro-magnetic actuators 120 arranged below the right part of the transport plane 110 can be operated in accordance with the sample container carrier calibration parameter of the sample container carrier 140 and their electro-magnetic actuator calibration parameters.

Hence, a respective electro-magnetic actuator 120, 120', 120" can be operated according to its first electric power supply parameter and the second electric power supply parameter of the corresponding sample container carrier 140, 140', 140", i.e. the electro-magnetic actuator 120, 120', 120" can be driven with the default driving voltage multiplied by the first electric power supply parameter and the second electric power supply parameter, when the electro-magnetic actuator 120, 120', 120" is activated.

Additionally or alternatively, it can be possible to compensate deviations regarding physical properties of the components of the laboratory sample distribution system 100 in other ways. For example, the electro-magnetic actuator calibration parameters of the electro-magnetic actuators 120, 120', 120" may comprise first activating time duration parameters and the sample container carrier calibration parameters of the sample container carriers 140, 140', 140" may comprise second activating time duration parameters. Hence a respective electro-magnetic actuator 120, 120', 120" can be operated according to its first activating time duration parameter and the second activating time duration parameter of the corresponding sample container carrier 140, 140', 140", i.e. the electro-magnetic actuator 120, 120', 120" can be driven with the default driving voltage for a default time duration multiplied by the first activating time duration parameter and the second activating time duration parameter.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method of operating a laboratory sample distribution system, the laboratory sample distribution system comprising a number of sample container carriers, the sample container carriers each comprising at least one magnetically active device and adapted to carry at least one sample container, a transport plane adapted to support the sample container carriers, and a number of electro-magnetic actuators stationary arranged below the transport plane, the electro-magnetic actuators adapted to move a corresponding sample container carrier on top of the transport plane by applying a magnetic force to the sample container carrier, the method comprising:
 a) activating one of the number electro-magnetic actuators to apply a magnetic force to one of the number of sample container carriers in order to cause a movement of the one sample container carrier;
 b) detecting an electro-magnetic actuator calibration movement profile of the one sample container carrier;
 c) determining at least one electro-magnetic actuator calibration parameter for the one electro-magnetic actuator in response to the electro-magnetic actuator calibration movement profile; and
 d) operating the one electro-magnetic actuator according to the at least one determined electro-magnetic actuator calibration parameter, when the one electro-magnetic actuator is activated a next time.

2. The method according to claim 1, wherein the steps a) to d) are executed for each of the number of electro-magnetic actuators.

3. The method according to claim 1, wherein the at least one electro-magnetic actuator calibration parameter comprises a first electric power supply parameter of the one electro-magnetic actuator.

4. The method according to claim 3, wherein in step d), the one electro-magnetic actuator is supplied with electric power according to the first electric power supply parameter.

5. The method according to claim 1, wherein the at least one electro-magnetic actuator calibration parameter comprises a first activating time duration parameter of the one electro-magnetic actuator.

6. The method according to claim 5, wherein in step d), the one electro-magnetic actuator is activated according to the first activating time duration parameter.

7. The method according to claim 1, further comprising, disqualifying the one electro-magnetic actuator,
if the at least one electro-magnetic actuator calibration parameter exceeds a specified electro-magnetic actuator parameter threshold value and/or
if a change of the at least one electro-magnetic actuator calibration parameter between at least two consecutive executions of the steps a) to c) exceeds a specified electro-magnetic actuator parameter change limit.

8. The method according to claim 1, wherein the steps performed during operating the one electro-magnetic actuator according to step d) are:
e) detecting a sample container carrier calibration movement profile of one of the number of sample container carriers;
f) determining at least one sample container carrier calibration parameter for the one sample container carrier in response to the sample container carrier calibration movement profile; and
g) operating the one electro-magnetic actuator according to the at least one determined sample container carrier calibration parameter.

9. The method according to claim 8, wherein each of the number of sample container carriers comprises a sample container carrier calibration parameter memory unit.

10. The method according to claim 9, further comprising,
storing the at least one sample container carrier calibration parameter on the sample container carrier calibration parameter memory unit; and
reading the at least one sample container carrier calibration parameter from the sample container carrier calibration parameter memory unit before step g).

11. The method according to claim 8, wherein the at least one sample container carrier calibration parameter comprises a second electric power supply parameter of the one electro-magnetic actuator.

12. The method according to claim 11, wherein in step g), the electro-magnetic actuator is supplied with electric power according to the second electric power supply parameter.

13. The method according to claim 8, wherein the at least one sample container carrier calibration parameter comprises a second activating time duration parameter of the one electro-magnetic actuator.

14. The method according to claim 13, wherein in step g), the electro-magnetic actuator is supplied with electric power according to the second activating time duration parameter.

15. The method according to claim 8, further comprising,
disqualifying the one sample container carrier,
if the at least one sample container carrier calibration parameter exceeds a specified sample container carrier parameter threshold value and/or
if a change of the at least one sample container carrier calibration parameter between at least two consecutive executions of the steps e) to f) exceeds a specified sample container carrier parameter change limit.

16. A laboratory sample distribution system adapted to perform the method according to claim 1, the laboratory sample distribution system comprising:
a number of sample container carriers, the sample container carriers each comprising at least one magnetically active device and adapted to carry at least one sample container;
a transport plane adapted to support said sample container carriers;
a number of electro-magnetic actuators stationary arranged below the transport plane, the electro-magnetic actuators adapted to move a corresponding sample container carrier on top of the transport plane by applying a magnetic force to the sample container carrier; and
a control unit adapted to activate one of the number of electro-magnetic actuators to apply a magnetic force to one of the number of sample container carriers to cause a movement of the one sample container carrier and to detect an electro-magnetic actuator calibration movement profile of the one sample container carrier and adapted to determine at least one electro-magnetic actuator calibration parameter for the one electro-magnetic actuator in response to the electro-magnetic actuator calibration movement profile and to operate the one electro-magnetic actuator according to the at least one determined electro-magnetic actuator calibration parameter, when the one electro-magnetic actuator is activated a next time.

17. The laboratory sample distribution system according to claim 16, wherein each of the number of sample container carriers comprises a sample container carrier calibration parameter memory unit for the at least one sample container carrier calibration parameter.

18. A laboratory automation system, the laboratory automation system comprising:
a number of a pre-analytical, analytical and/or post-analytical laboratory stations; and
a laboratory sample distribution system according to claim 16 adapted to distribute the sample container carriers and/or sample containers between the laboratory stations.

* * * * *